United States Patent
Gorges et al.

(10) Patent No.: US 7,559,694 B2
(45) Date of Patent: Jul. 14, 2009

(54) METHOD FOR ACQUISITION GEOMETRY OF AN IMAGING SYSTEM

(75) Inventors: Sébastien Gorges, Nancy (FR); Yves Lucien Trousset, Palaiseau (FR); Jérémie Pescatore, Le Chesnay (FR); Erwan Kerrien, Nancy (FR); Marie-Odile Berger, Maron (FR); Régis Vaillant, Villebon dur Yvette (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/293,940

(22) Filed: Dec. 5, 2005

(65) Prior Publication Data

US 2007/0172033 A1    Jul. 26, 2007

(30) Foreign Application Priority Data

Dec. 17, 2004    (FR)    ................. 04 53054

(51) Int. Cl.
*G01D 18/00*    (2006.01)
(52) U.S. Cl. .................... 378/207; 378/205
(58) Field of Classification Search ............ 378/4, 378/205, 207, 901
See application file for complete search history.

(56) References Cited

U.S. PATENT DOCUMENTS

| | | | | |
|---|---|---|---|---|
| 5,442,674 A * | 8/1995 | Picard et al. | ............... | 378/20 |
| 5,936,612 A * | 8/1999 | Wang | ............... | 345/164 |
| 5,963,613 A * | 10/1999 | Navab | ............... | 378/4 |
| 6,038,282 A * | 3/2000 | Wiesent et al. | ............... | 378/62 |
| 6,049,582 A * | 4/2000 | Navab | ............... | 378/4 |
| 6,206,566 B1 * | 3/2001 | Schuetz | ............... | 378/205 |
| 6,379,043 B1 * | 4/2002 | Zylka et al. | ............... | 378/207 |
| 6,466,638 B1 * | 10/2002 | Silver et al. | ............... | 378/4 |
| 6,533,455 B2 * | 3/2003 | Graumann et al. | ............... | 378/205 |
| 6,851,855 B2 * | 2/2005 | Mitschke et al. | ............... | 378/207 |
| 2001/0053204 A1 * | 12/2001 | Navab et al. | ............... | 378/205 |
| 2004/0202288 A1 * | 10/2004 | Pescatore et al. | ............... | 378/207 |
| 2006/0039537 A1 * | 2/2006 | Strobel | ............... | 378/197 |

FOREIGN PATENT DOCUMENTS

WO    WO 03/084380 A2    10/2003

OTHER PUBLICATIONS

Silver et al., Determination and correction of the wobble of a C-arm gantry, In Medical Imgaing 2000: Image Processing, Proceedings of SPIE vol. 3979, 2000.*
Strobel et al., Improving 3D Image Quality of X-ray C-Arm Imaging Systems by Using Properly Designed Pose Determination Systems for Calibrating the Projection Geometry, Medical Imaging 2003: Physics of Medical Imaging, pp. 943-954.*
Wiesent et al., Enhanced 3-D-Reconstruction Algorithm of C-Arm Systems Suitable for Interventional Procedures, IEEE Transactions On Medical Imaging, vol. 19., No. 5, May 2000, pp. 391-403.*

(Continued)

*Primary Examiner*—Edward J Glick
*Assistant Examiner*—Alexander H Taningco
(74) *Attorney, Agent, or Firm*—Global Patent Operation (57) ABSTRACT

A method for determining acquisition geometry of an imaging system from a set of calibration matrices for an arbitrary position of the system, a projection matrix makes a point in a 2D image correspond to a point of an object in a space. This matrix is produced for any unspecified position of the system from knowledge of a limited number of pre-computed calibration matrices. For instance, a projection matrix may be computed by interpolating coefficients of calibration matrices and/or applying a transformation with a rigid model defined comprehensively or locally to a particular calibration matrix.

7 Claims, 5 Drawing Sheets

OTHER PUBLICATIONS

Kerrien et al,, "Machine Precision Assessment for 3D/2D Digital Subtracted Angiography Images Registration", Proc. SPIE, vol. 3338, Feb. 1998, pp. 39-49.

Canero e tal., "Modeling the Acquisition Geometery of a C-Arm Angiography System for 3D Reconstruction", CCIA 2002, LNAI 2504, pp. 322-335.

Mitschke et al., Optimal configuration for dynamic calibration of projection geomettry of Xray C-arm Systems, IEEE 2000.

Erwan Kerrien, "Outils d'imgerie multimodalite pour la neuroradiologie interventionnelle", PhD thesis, INPL, Jan. 2000; accessible at http://www.loria.fr/-kerrien/these.html.

* cited by examiner

METHOD FOR ACQUISITION GEOMETRY OF AN IMAGING SYSTEM

CROSS-REFERENCE TO RELATED APPLICATIONS

This application claims the benefit of a priority under 35 USC 119(a)-(d) to French Patent Application No. 04 53054 filed Dec. 17, 2004, the entire contents of which are hereby incorporated by reference.

BACKGROUND OF THE INVENTION

An embodiment of the present invention relates to a method and apparatus for determining acquisition geometry of an imaging system, as a function of parameters of the system, for an arbitrary position. An embodiment of the invention is more particularly directed to a method and apparatus for medical imaging. An embodiment of the invention is directed to providing greater precision and robustness to a geometry-determining operation of this kind. An embodiment of the invention can be applied to but not exclusively in the field of radiology and in particular to X-ray systems implementing methods of tomography or tomodensitometry.

There are known radiology systems that comprise a source of radiation, such as an X-ray tube, and a detector of the radiation, such as an X-ray detector, a table or support and a C-type arm, such as C-shaped arm or C-arm that is generally a vascular C-arm. These systems are capable of shifting in all three dimensions of a space. This mobility enables the practitioner to acquire images for any part whatsoever of the body of an object such as a patient lying on the table. In general, the table is capable of shifting in the three possible motions of translation associated with a given space, while the C-type arm is capable of shifting in the three possible rotations associated with this space. The practitioner uses a system of interventional radiology to have available tools such as a catheter or a coil within the patient's body, especially in the head. The geometry of the acquired images must be known with precision in order to help the practitioner in the positioning of the tools.

Two types of image acquisition are possible with these systems. The practitioner may acquire 2D images obtained by the projection of X-rays on the detector. Each image is obtained for a given position of the tube and of the detector. The part of the patient's body is then projected on the detector, in a conical projection. To guide these tools during a procedure, the practitioner may thus use these 2D images obtained with or without any contrast agent. The images acquired with low doses of X-rays are called fluoroscopy images. The practitioner can also acquire 3D images. During the acquisition of the images, the tube and the detector move about the patient, in a rotation of 40 degrees per second for example, in theory covering at least 194 degrees. Several projected images are then acquired by the C-type arm and, from these images, the part of the body to be viewed may be reconstructed in three dimensions. The contrast of these 3D images may be improved through an injection of a contrast agent.

The fluoroscopy images are acquired in real-time while the 3D image, which is generally a pre-operation image, is fixed. To improve the tool guidance system, there is a prior art method of projecting the 3D image on the fluoroscopy image. This method is called 3D enhanced fluoroscopy. It is also possible to project a 3D image on a pre-operation 2D image, for example a DSA image. There is also a prior art method whereby, in reverse, the 2D image is back-projected on the 3D image. This method is called the 3D roadmap method.

The difficulty of implementing these methods lies in the merging of the two images in taking account of the right acquisition geometry of the system. When projecting the 3D image on the 2D image or vice versa, it should be possible to determine the acquisition geometry of the imaging system whatever the position of this system in space. The acquisition geometry of the system is relative to the positioning of the tube and detector in a given reference system. This acquisition geometry is defined by the spatial position of both the C-type arm and the table, relative to a given referential system. The degree of freedom of the table can be modeled without great difficulty, by the use of prior art models. The C-type arm is more difficult to model.

A considerable effort is made to compute projection matrices that make a point located in the 2D image correspond to a point located in the reconstructed 3D image. A pixel of the 2D image is supposed to correspond to the projection of a 3D voxel of the reconstructed 3D image on the X-ray detector, in as much as this image will have been placed on the body. It should be possible to produce one projection matrix for each position of the C-type arm in space. This projection matrix is associated with the acquisition geometry of the system.

The method described in WO03/084380 proposes to integrate information produced by sensors of the vascular C-type arm into a rigid model of the C-type arm, in order to produce the projection matrices. The thesis by Erwan Kerrien, "Outils d'imagerie multimodalité pour la neuroradiologie interventionnelle" (Multi-Modality imaging tools for interventional neuroradiology), describes a method in which the projection matrices are computed from a calibration of positions of the C-type arm and the computation of a certain number of geometry parameters. At the SPIE *Medical Imaging* 98 conference in San Diego, USA, February 1998, Erwan Kerrien et al. in "Machine precision assessment for 3D/2D digital subtracted angiography images registration", proposed a method pertaining to subtractive angiography. FR-2848806, describes a method for the calibration of a radiology imaging apparatus requiring a limited number of acquisitions. This method is based on a linear interpolation of matrix parameters of calibration matrices. This calibration method works only for the calibration of an axis of the C-arm, with the aim of a 3D image reconstruction. In "Optical configuration for dynamic calibration of projection geometry of X-ray C-arm systems", Nassir Navab describes a method in which a CCD camera is attached to the X-ray detector. In this method, the geometry of the camera is used to compute the projection matrix. It is a method of measurement and not a method for the prediction of the projective matrix. In "Modeling the acquisition geometry of a C-arm angiography system for 3D reconstruction", Cristina Canero et al. model the C-type arm in considering the intrinsic parameters of the projection matrix to be constant.

However, these prior art methods have limits as regards the modeling of the C-type arm. For the results of the projection of a point in space on the 2D image are not sufficiently precise. These methods are generally based on a rigid model of the C-type arm with constant internal parameters. This rigid model assumes the existence of unique axes of rotation about which the C-type arm is likely to rotate. However as a result of mechanical distortion undergone by the C-type arm and play between certain parts of the medical system, this rigid model, which may be called an ideal model, is often put at fault and the results obtained are not sufficiently precise for medical applications such as angiography. In particular, the theoretical nature of the trajectory of the ends of the C-type arm does not take account of the (great) weight of the X-ray tube and/or of the detector that causes this C-type arm to sag in proportions that are always variable.

BRIEF DESCRIPTION OF THE INVENTION

An embodiment of the invention is directed to resolving these problems of precision of the existing methods. An embodiment of the invention therefore relates to a method and apparatus for acquisition geometry of an imaging system in which a computation is made of a projection matrix associated with any unspecified acquisition position of the system about an object placed on a support, such as a table; the projection matrix setting up a correspondence, for a given incidence of radiation, of a position of a point of the object with an information content assigned to projection pixels in a 2D image; and for computation of the projection matrix, one or more projection matrices, called calibration matrices, are pre-computed, each calibration matrix being associated with a calibration position of the system.

BRIEF DESCRIPTION OF THE DRAWINGS

An embodiment of the invention will be understood more clearly from the following description and the accompanying figures. These figures are given by way of an illustration but in no way restrict the scope of the invention. Of these figures.

DETAILED DESCRIPTION OF THE INVENTION

An embodiment of the invention takes into account the mechanical distortion of the C-type arm to compute the acquisition geometry of the system. Thus, the method of an embodiment of the invention is based on the assumption that the distortions of the C-type arm relative to the rigid model are predictable and repeatable. As a consequence, a geometrical model that takes account of the distortion of the C-type arm is built and, on the basis of this model, the acquisition geometry of the imaging system is computed for any position of this system as a function of position parameters obtained from the sensors of the system. The geometrical model used to set up a model of an acquisition geometry that may evolve as a function of the position of the system. It may be considered that, unlike in the known methods, internal parameters of the system vary as a function of the position of this system.

The acquisition geometry of the system may thus be estimated from any position whatsoever of the C-type arm, on the basis of knowledge of a limited number of calibration positions. A known calibration position is a position for which the acquisition geometry of the C-type arm has been determined in projecting X-rays on a calibration phantom. A calibration phantom is a geometrical element of a particular shape whose conformation in space is known with exactness and for which the reconstructed image that it must result in is known a priori. For a calibration position, the projection matrix is therefore perfectly known. Since the number of calibration positions is limited, the method of an embodiment of the invention is simple to implement.

It is possible to keep the simplicity of the rigid model while at the same time locally adjusting some of its parameters so as to approach the real behavior of the C-type arm. One embodiment for implementation of the method of the invention entails calibration of the rotation axes and, optionally, an isocenter of the rigid model associated with the C-type arm. The isocenter is defined by the intersection of all three axes. A calibration matrix corresponding to a particular position of the C-type arm, called a calibration position, is then determined.

Furthermore, a rigid transformation is applied to this calibration matrix for obtaining a projection matrix for any position whatsoever of the system in space. The rigid transformation corresponds to rotations and translation motions of the C-type arm. This transformation is built from values of angles made by the C-type arm with the three axes and also generally from a distance between the tube and the detector. These values of angles and this distance are generally acquired through sensors of the medical system.

As a variant embodiment, the parameters of the calibration matrix are interpolated geometrically between calibration positions.

As a variant embodiment, corrective terms are introduced within the rigid model.

As a variant embodiment, parametric models, known as elastic models, of the projection matrix are produced from experimental measurements and/or from known mechanical characteristics of the vascular ring.

Naturally, the different variants can be combined with one another in order to further augment the precision of the results obtained.

For reasons of simplicity, the embodiments of implementation of the invention are described for systems known as monoplane type systems. A system of this type generally has a plane associated with a C-type arm that is mobile in all directions of a space. However, the calibration of a biplane system can also be done by calibrating the two planes of the system separately. These two planes are generally associated with two C-type arms that are mobile in all the directions of space.

Figure 1:
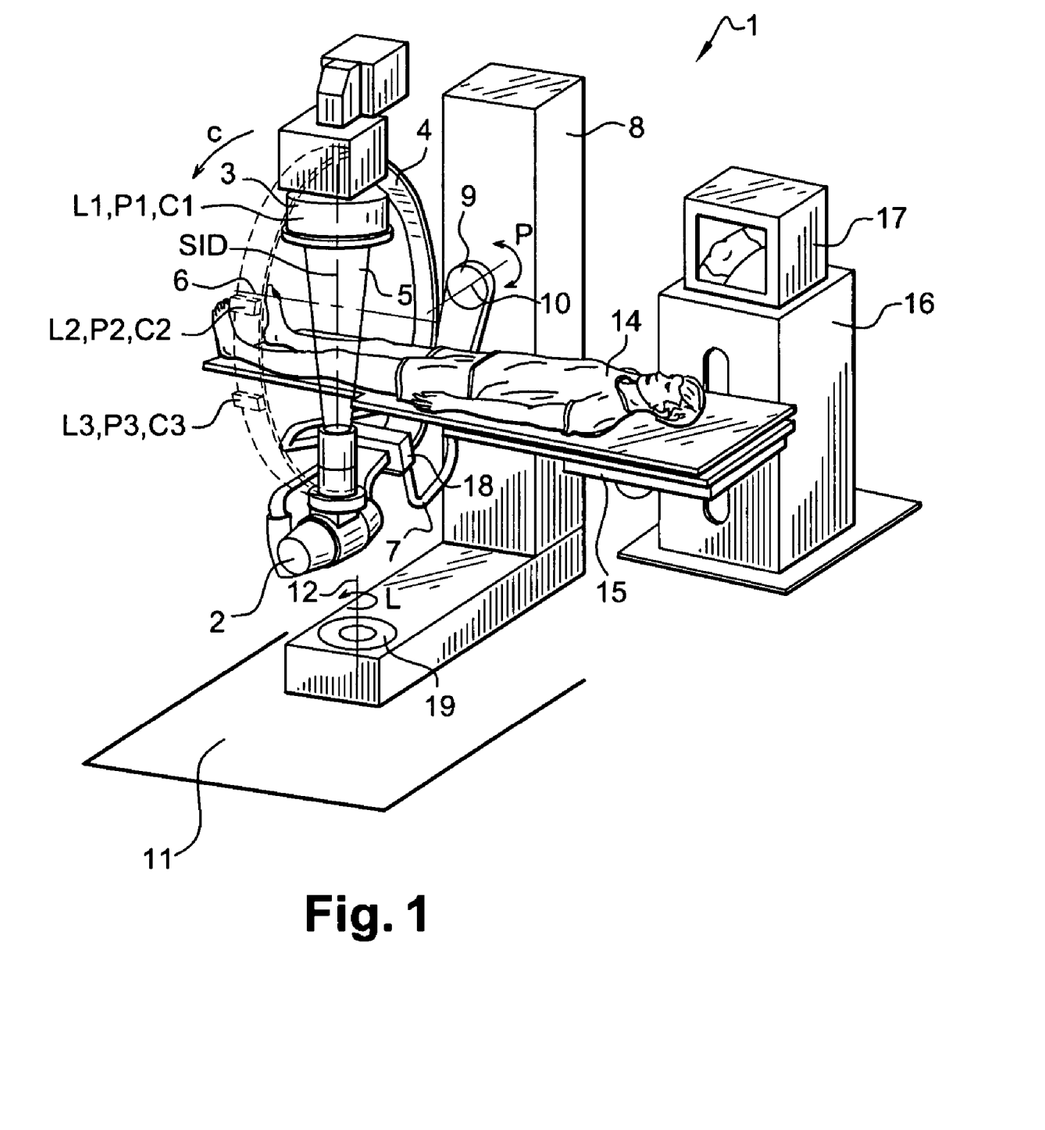
FIG. 1 is a schematic representation of an imaging X-ray system that can be used with an embodiment of the method of the invention.

FIG. 1 shows an imaging system 1 that may be used with an embodiment the method according to the invention. This system 1 comprises an X-ray tube 2 and an X-ray detector 3 hooked to a C-type arm 4. A patient 14 reclines on a table 15. This table 15 is positioned between the tube 2 and the detector 3. The detector 3 is positioned so that a main direction of emission of the rays 5 is on the whole perpendicular to a face of the detector 3. The table 15 is connected to a base 16 on which a computer system 17 is placed. This computer system 17, whose working is described in detail in FIG. 2, enables the acquisition and display of 2D or 3D images.

More specifically, the C-type arm 4 is liable to rotate about an axis 6. This axis 6 is perpendicular to a surface demarcated by the C-type arm 4, and passes through the middle of a segment demarcated by the emitter 2 and the detector 3. The C-type arm 4 is connected to an intermediate arm 7 by means of a sliding link 18. The intermediate arm 7 is capable of rotating about an axis 10 that is on the whole perpendicular to a face of an L-shaped pedestal 8. The intermediate arm 7 is connected to the pedestal 8 by means of a rotating link 9. The pedestal 8 is liable to turn about an axis 12 that is perpendicular on the whole to a ground 11. The pedestal 8 is connected to the ground 11 by means of rotating link 19.

The C-type arm 4 is therefore able to rotate about the three axes 6, 10 and 12 which form a reference system. A position of the C-type arm 4 can therefore be identified in the reference system by three angles L, P, and C that can be formed by this C-type arm 4 respectively with the axes 6, 10 and 12, relative to a reference position. The position of the C-type arm 4 is also defined by a distance SID between the tube 2 and the detector 3.

To set up a model of the motions of the C-type arm 4 in space, a rigid model is used. In this rigid model, the C-type arm 4 may be considered in an ideal way. This C-type arm 4 is in this case rigid, the tube 2 and the detector 3 are rigidly attached to this C-type arm 4, and motions of this C-type arm 4 may be described by perfect rotations about the three axes 6, 10 and 12. It is also considered to be the case that internal parameters of the system relating especially to a positioning of the tube 2 and of the detector 3 are constant. The three axes 6, 10 and 12 may be considered to intersect at a point called an isocenter, but this hypothesis is not necessary in the definition of the rigid model. A reference system having axes that intersect at a point is called an isocentric reference system.

Starting from a defined model of the C-type arm 4, a computation is made of the acquisition geometry of the system for an arbitrary position of the system defined by the parameters L, P and C. These parameters may be measured by means of position sensors (not shown) located at the position of the mobile links 10, 18, 19. Electrical signals coming from the sensors may be sent to the computer system 17.

Figure 2:
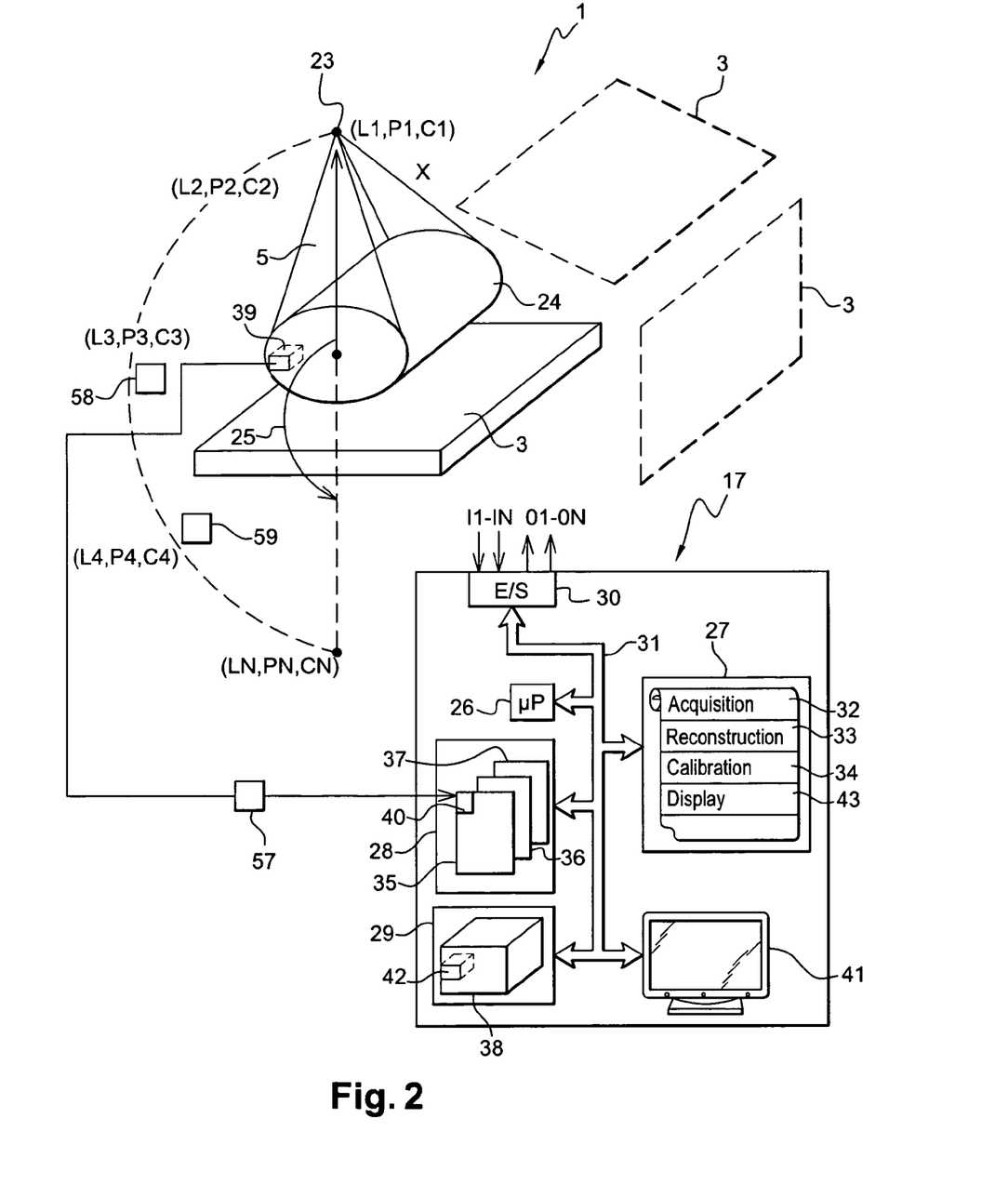
FIG. 2 is a schematic representation of an embodiment for implementation of the invention.

FIG. 2 shows an exemplary image acquisition using the X-ray system 1. The tube 2 and detector 3 are located on either side of a 3D object 24. The tube 2 is a conical source of X-rays 5. The X-rays are projected on the detector 3 after penetration of the object 24. The detector 3 has sensors that measure the intensity of the rays that it receives. The tube 2 is for example of capable of making a rotation of at least 180 degrees, along a direction 25, about the object 24. In general, the tube 2 is capable of rotating about the object 34 in any unspecified direction.

The computer system 17 has a microprocessor 26. The microprocessor 26 is connected to a program memory 27, data memories 28 and 29, an input-output interface 30 and a screen 41, by means of a communications bus 31. The input-output interface 30 sends output signals O1-ON to the imaging system 1 and receives input signals I1-IN sent out by the imaging system 1.

When the microprocessor 26 executes an acquisition program 32, output signals may be sent out so as to position the tube 2 in a particular position. Other output signals may also be sent out to the tube 2 to command the sending of the X-rays. One or more images 35-37 in 2D projection may then be acquired for different angles of incidence of X-rays. For example, the acquisition of 2D images may be made for the positions of the C-type arm 4 referenced (L1, P1, C1)-(LN, PN, CN). Information contents on the 2D images 35-37 are stored inside the memory 28. These information contents on the intensity of the received X-rays are associated with projection pixels 40 of the images 35-37.

A projection matrix 57 is associated with each acquisition position (L1, P1, C1)-(LN, PN, CN) of the C-arm 4. Matrix 57 brings about the correspondence, with a point 39 of the object 24, of an information content assigned to projection pixels 40 in a 2D image acquired for a given position of the C-type arm 4. The microprocessor 26 computes a projection matrix associated with any unspecified position of acquisition of the system about the object 24 as a function of the parameters L, P and C coming from the sensors of the medical system 1. More specifically, a projection matrix 57 may be subdivided into two sets of geometrical parameters: intrinsic parameters and extrinsic parameters. The intrinsic parameters correspond to projection parameters of the X-ray tube 2 on a projection image or, more specifically, on the X-ray detector 3. The extrinsic parameters correspond to a general position of the imaging system defined by rotations and translation motions of this system, in a given reference system.

The projection matrix is produced for a given position of the C-type arm 4 by means of a limited number of pre-computed projection matrices 58, 59 to be called calibration matrices. These calibration matrices 58, 59 are computed for particular positions of the system, called calibration positions. In general, at least one calibration matrix 58, 59 is computed. In one example, certain of the acquisition positions (L1, P1, C1)-(LN, PN, CN) are calibration positions. In one example, between ten and thirty calibration positions are determined. Each calibration position may have several calibration matrices corresponding to it as will be seen in FIGS. 7a and 7b. In another example, between ten and thirty calibration matrices are pre-computed.

To determine the calibration matrices, the microprocessor 26 may execute a calibration program 34. This program 34 is executed after the practitioner has an element 24 of a known shape, called a phantom, available on the table 15. In one implementation, the phantom, as shown in FIG. 7b, is formed by beads for which the conformation in space is known with precision. After the phantom has been positioned, X-rays are projected with a given incidence on the detector 3 and are revealed by one of the images 35-37 in 2D projection with projection pixels 40. The calibration matrix that makes an information content assigned to projection pixels correspond to a point of the phantom is then computed.

The microprocessor 26 can also execute a reconstruction program 33 in which a final volume image 38 is reproduced from 2D images. Information contents of this image 38 are stored within the memory 29. These information contents are stored at memory addresses that correspond to voxels 42 of the image 38. This reconstruction program may comprise a display sub-program 43 that is used to display the information content of the voxels on the screen 41. In one particular application, the image 38 may be combined with 2D images using projection matrices 57.

Figure 3:
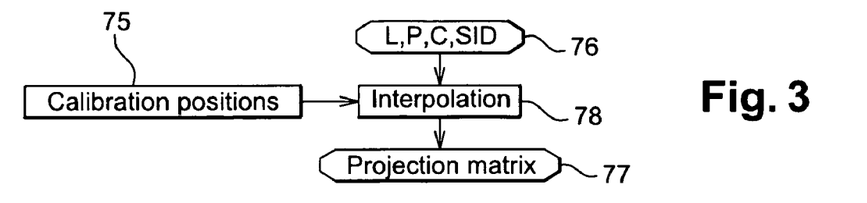
FIG. 3 is a diagram of a variant of the method according to an embodiment of the invention in which coefficients of calibration matrices are interpolated.

FIG. 3 shows a diagram of steps 75-77 of the method according to an embodiment of the invention. In the step 75 several calibration matrices are computed for different calibration positions. From one calibration position to another, the angles L, P and C vary. If necessary, it is also possible to obtain a variation in the distance SID from one calibration position to another. The projection matrix 77 is produced for any unspecified position 76 of the C-type arm 4, as a function of the calibration matrices. To produce the projection matrix associated with any unspecified position 76 of the C-type arm 4, the parameters of the calibration matrices are interpolated in a step 78. In other words, to predict any projection matrix 77 whatsoever, the parameters of the calibration matrices and/or corresponding geometrical parameters are interpolated between the calibration positions.

Figure 4:
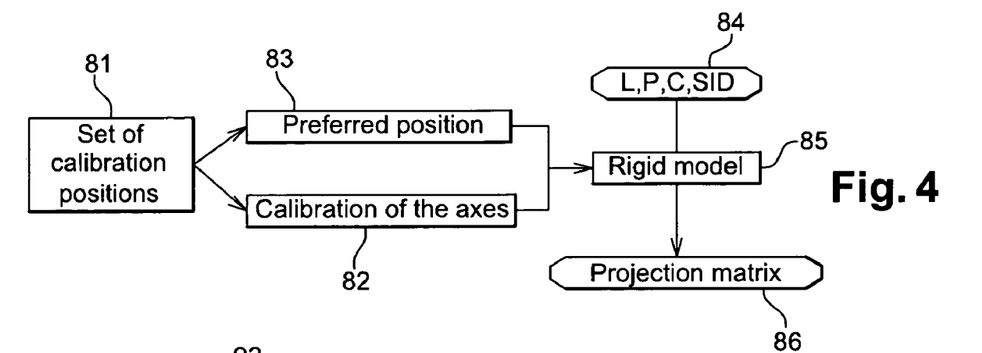
FIG. 4 is a diagram of a variant of the method according to an embodiment of the invention in which preferred positions of calibration are defined.

FIG. 4 shows a schematic view of steps of a variant embodiment of the invention. In this variant embodiment, a set of calibration matrices is always computed for different calibration positions in step 81. The above-mentioned rigid model calibrated in step 82 is considered here. In step 82 the axes and, as the case may be, the isocenter of the rigid model are calibrated by using a phantom. This embodiment may be implemented with models comprising axes that do-not intersect at a point. In step 85, a rigid transformation is applied to a calibration matrix associated with a preferred position. The rigid transformation corresponds to a shift of the rigid model. The preferred position is computed in step 83. The preferred position is for example the calibration position closest to the position 84 of the C-type arm. The projection matrix 86 associated with the unspecified position 84 of the C-type arm 4 is then obtained. As a variant embodiment, the preferred position corresponds to a position for which the parameters of the calibration matrices have been interpolated. As a variant embodiment, only one calibration matrix is pre-computed.

Figure 5:
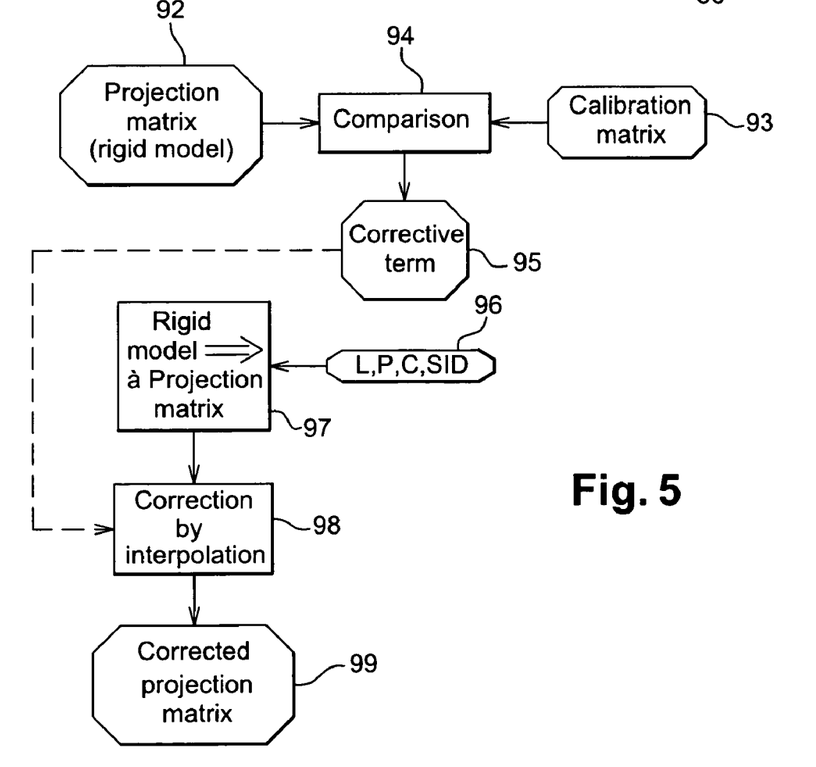
FIG. 5 is a diagram of a variant of the method according to an embodiment of the invention in which a correction term is introduced.

FIG. 5 shows a diagram of steps of a variant embodiment of the method according to the invention. This variant embodiment introduces a corrective term within the rigid model. This corrective term is used to take into consideration a distortion undergone by the C-type arm 4. In this variant embodiment, for each calibration position, a distortion of the C-type arm 4 is estimated by comparing the projection matrix 92, obtained by means of the rigid model, and the calibration matrix 93 that is considered to be the standard projection matrix. The comparison of these two matrices 92 and 95 is done in step 94. A basic corrective term 95 is then deduced therefrom for each calibration position. This basic corrective term 95 corresponds to a residual rigid transformation enabling passage from the calibration matrix 93 to the projection matrix associated with the rigid model. In step 97, the projection matrix for any unspecified position 96 of the C-type arm 4 is computed by means of the rigid model. In step 98, the projection matrix obtained is corrected by means of a corrective term. This corrective term is produced by interpolation of the basic corrective terms associated with the calibration matrices closest to the position 96. A corrected projection matrix 99 is then obtained. The introduction of the corrective term augments the precision of the rigid model. This corrective term may of course be introduced into every variant embodiment of the method according to the invention.

Figure 6:
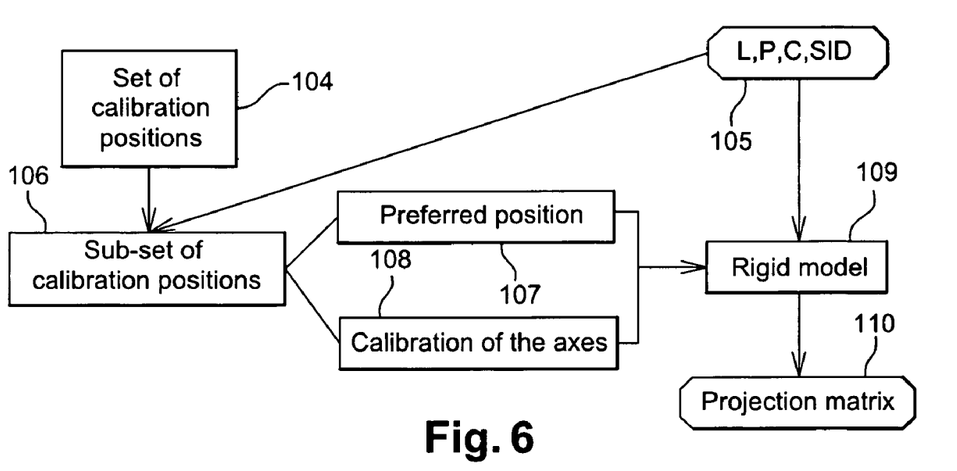
FIG. 6 is a diagram of a variant of the method according to an embodiment of the invention in which sub-sets of calibration positions are defined.

FIG. 6 is a diagram of steps of a variant embodiment of the method according to the invention. In step 104, a set of calibration matrices associated with a set of calibration positions is pre-computed as hereinabove. In step 106, sub-sets of calibration positions are defined. In one example, the calibration positions of a sub-set are close to one another from a geometrical point of view. Angular differences associated with calibration positions of a sub-set may be smaller than a threshold angular value, for example a value of 10 degrees. In this example, the rigid model is defined for each sub-set. Thus parameters of the rigid model, such as for example a position of the rotation axes 6, 10, 12 that are associated with it and/or the coordinates of its isocenter, are computed locally for each calibration position, using a sub-set of calibration positions. For any unspecified position 105 of the C-arm defined by the parameters L, P, C and SID, a preferred position 107 is defined, corresponding for example to the calibration position closest to the position 105. Furthermore, the axes, and optionally the isocenter, of the model of the sub-set corresponding to the preferred position, are calibrated in step 108. The calibration of the isocenter is optional because, in certain variants, it is possible to use a model defined by axes that do not intersect at a point (there is then no isocenter). For any unspecified position 105 of the C-type arm 4, the projection matrix 110 is produced by using the local rigid model associated with the calibration position closest to this position 105. Thus, for a position 105, it is possible to produce the projection matrix from a local, calibrated rigid model that most closely approaches the behavior of the C-type arm 4 right on the position 105.

Figure 7A:
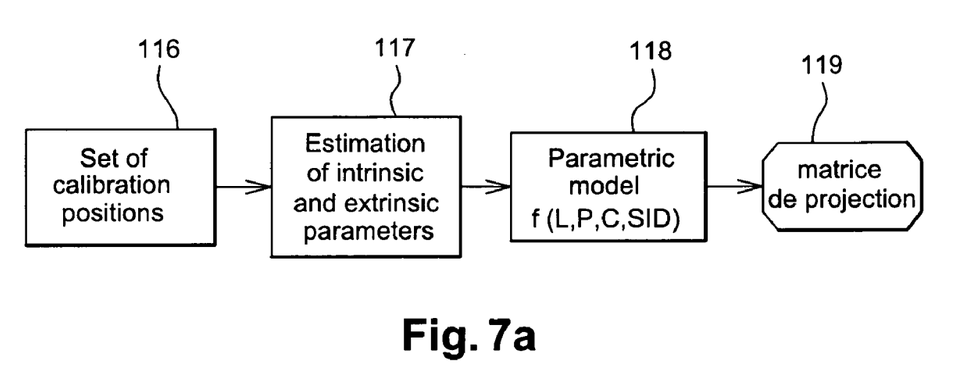
FIGS. 7-8 are diagrams of variants of the method according to an embodiment of the invention in which particular parametric models of a projection matrix are prepared.
Figure 7B:
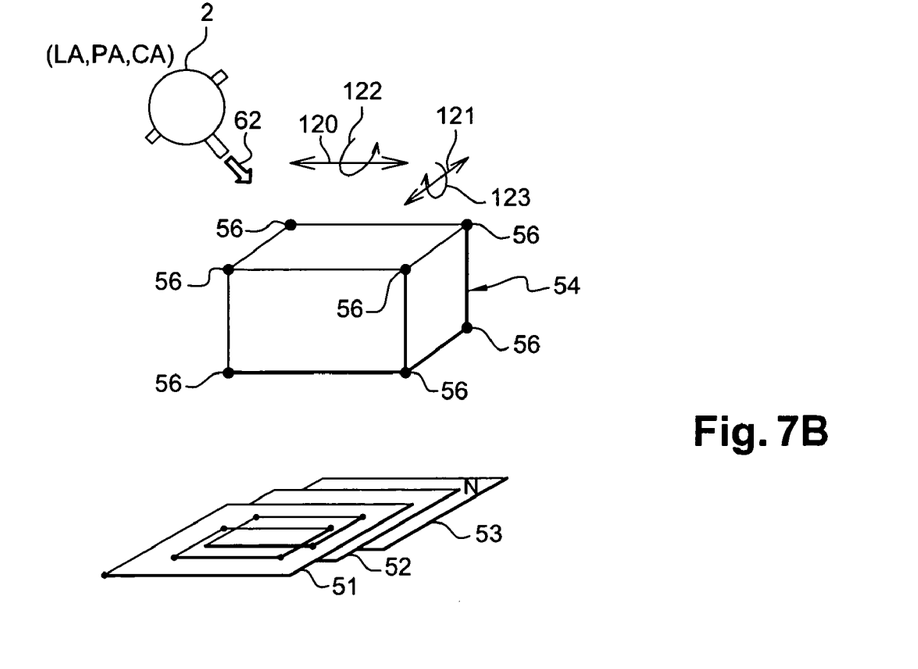

FIG. 7a is a diagram of steps of a variant embodiment of the method according to the invention. In step 116, pre-computed calibration matrices are produced. In step 117, for each calibration position, intrinsic and extrinsic parameters of the calibration matrix are computed. As shown in FIG. 7b, for each calibration position, a number N of calibration images 51-53 is acquired by shifting the calibration phantom 54 in translation 121, 122 and in rotation 122, 123 from one image to another. Thus, for a given calibration position (LA, PA, CA) with which a given X-ray incidence 62 is associated, N 2D images 51-53 is acquired. Since the C-type arm 4 does not move, the intrinsic parameters are constant whatever the position of the calibration phantom 54. A beam adjustment technique is then used to calibrate the N images corresponding to a fixed position of the C-type arm 4. More specifically, in this technique, initially N projection matrices corresponding to the N images are computed with a constraint that dictates identical intrinsic parameters for the N projection matrices. The intrinsic parameters are thus computed robustly. These intrinsic parameters are computed from N different positions of the calibration phantom 54, whereas, in classic methods, they are estimated from only one position.

In a further stage, the extrinsic parameters are computed for each calibration position. Since the intrinsic parameters are known precisely, the computation of the extrinsic parameters of the calibration matrices is also robust.

In step 118 shown in FIG. 7a, a parametric model is produced. The parametric model describes the evolution of the intrinsic and extrinsic parameters of the projection matrix as a function of the configuration of the C-type arm 4. The configuration of the C-type arm 4 is defined by the angles L, P and C and the distance SID. The parametric model is thus produced as a function of the evolution of the parameters from one calibration position to another. The projection matrix 119 can then be produced for any unspecified position of the C-type arm 4 by simple application of the parametric model obtained. The parameters of the model are then replaced by real values of the position of the C-type arm 4. This variant embodiment of the method takes account of the distortion of the C-type arm 4 by incorporating them into the parametric model. This method does not generally necessitate any a priori information on the distortion of the C-type arm 4. This embodiment of the method may be combined with the other variants of the method according to the invention, especially the method of FIG. 8.

Figure 8:
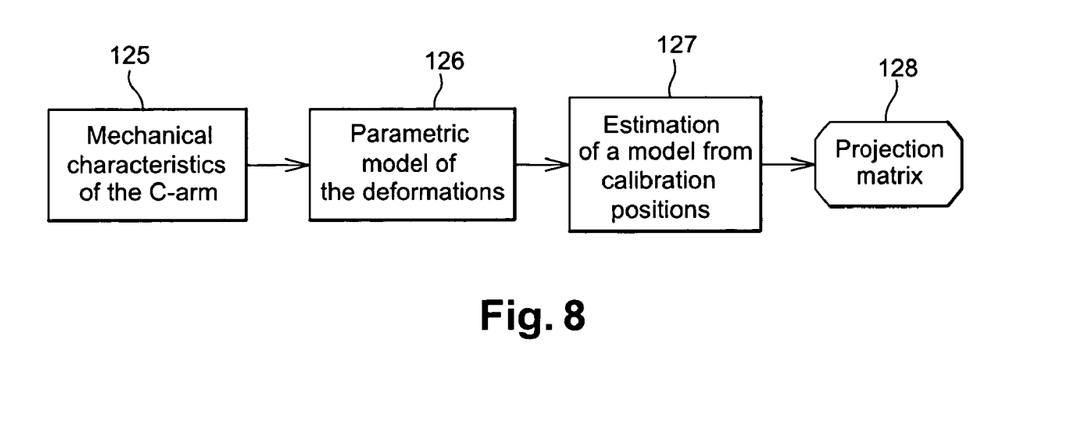

FIG. 8 shows a diagram of steps of another variant embodiment of the method according to the invention. In this variant embodiment, known mechanical characteristics 125 of the C-type arm 4 are introduced into a parametric model 126 of the distortions. This parametric model, built in step 126, takes into account the distortions due to a bending and a rotational shift of the pedestal 8, as well as a tilt of the tube 2. Distortions of the C-type arm 4 and/or of the detector 3 may also be taken into account. These distortions are due especially to gravity and to mechanical clearance between parts. These distortions are a function of the position of the C-type arm 4 in space. This position is defined by the parameters L, P, C and SID. The distortions taken into account in this parametric model are generally predictable and repeatable in time. In a particular implementation, the above-mentioned distortions are modeled by translation motions and rotation that are a function of the parameters L, P, C and SID. The parameters of the model are then adjusted by means of a set of calibration positions in step 127. Step 127 is thus used to adjust the general model of the distortions to a C-arm 4 of a particular system. By applying the parametric model of the projection matrices to a given position of the C-type arm, it is possible to produce the projection matrix 128 associated with this position.

In general, in the embodiments of invention, the interpolation models used may be linear or non-linear. In certain cases, the interpolation taking account of the closest neighbor may be used. Depending on the variant embodiment of the method implemented, the interpolation may be done directly on the coefficients of the projection matrix or on fundamental geometric parameters.

The method of the embodiments of the invention is preferably implemented with a method of 3D enhanced fluoroscopy method and/or the 3D roadmap method.

In addition, while an embodiment of the invention has been described with reference to exemplary embodiments, it will be understood by those skilled in the art that various changes may be made in the function and/or way and/or result and equivalents may be substituted for elements thereof without departing from the scope and extent of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. or steps do not denote any order or importance, but rather the terms first, second, etc. or steps are used to distinguish one element or feature from another. Furthermore, the use of the terms a, an, etc. do not denote a limitation of quantity, but rather denote the presence of at least one of the referenced element or feature.

What is claimed is:

1. A method of determining an acquisition geometry of an imaging system having a source of radiation and a C-type arm capable of shifting about three axes of rotation around an object, the method comprising:
    computing a calibration matrix for a calibration position of the imaging system;
    producing a projection matrix for an unspecified acquisition position of the C-type arm as a function of the calibration matrix, wherein the projection matrix brings about correspondence of a point of the object with an information content assigned to at least one projection pixel in a 2D image obtained at the unspecified acquisition position of the C-type arm;
    estimating a distortion undergone by the C-type arm at the calibration position by comparing the calibration matrix with the projection matrix to deduce a basic corrective term;
    computing a corrective term of the projection matrix for the unspecified acquisition position of the C-type arm by interpolating the basic corrective term; and
    correcting the projection matrix for the unspecified acquisition position of the C-type arm with the computed corrective term.

2. The method of claim 1, wherein the step of computing a calibration matrix is based on a measured parameter, wherein the measured parameter is one of:
    (a) a distance between an X-ray tube and a corresponding X-ray detector,
    (b) one or more angles formed by the C-type arm with respect to one or more respective axes relative to a reference position, and
    (c) a combination of parameter (a) and parameter (b).

3. The method of claim 2, wherein the step of producing a projection matrix further comprises:
    interpolating the measured parameter between two calibration positions of the imaging system.

4. The method of claim 1, farther comprising:
    interpolating basic corrective terms associated with calibration matrices closest to the unspecified acquisition position to deduce a second basic corrective term for the projection matrix for the unspecified acquisition position; and
    correcting the projection matrix for the unspecified acquisition position with the second basic corrective term.

5. The method of claim 1, wherein the calibration matrix comprises: at least one intrinsic parameter, wherein the at least one intrinsic parameter corresponds to at least one projection parameter of an X-ray tube on a corresponding X-ray detector.

6. The method of claim 1, wherein the calibration matrix comprises: at least one extrinsic parameter, wherein the at least one extrinsic parameter corresponds to a general position of the imaging system as defined by a rotation and a translation motion of the imaging system in a predetermined reference system.

7. The method of claim 1, further comprising:
    obtaining, for the calibration position, a number N of calibration images by shifting a calibration phantom in translation and in rotation from one calibration image to another.

* * * * *